United States Patent [19]
Kalnes et al.

[11] Patent Number: 5,744,669
[45] Date of Patent: Apr. 28, 1998

[54] PROCESS FOR THE CONVERSION OF A HALOGENATED ORGANIC STREAM CONTAINING TRACE QUANTITIES OF ORGANIC NITRATES

[75] Inventors: Tom N. Kalnes, La Grange; George R. Hibel, Schaumburg; Chwu-Ching Jan, Elk Grove Village, all of Ill.

[73] Assignee: UOP, Des Plaines, Ill.

[21] Appl. No.: 792,587

[22] Filed: Jan. 30, 1997

Related U.S. Application Data

[63] Continuation-in-part of Ser. No. 388,112, Feb. 13, 1995, Pat. No. 5,600,041, which is a continuation-in-part of Ser. No. 192,532, Feb. 7, 1994, abandoned, which is a continuation-in-part of Ser. No. 981,962, Nov. 25, 1992, abandoned.

[51] Int. Cl.⁶ .............................. C07C 4/00; C07C 17/38
[52] U.S. Cl. .......................... 585/310; 585/312; 585/733; 570/180; 570/177; 570/211; 570/213; 570/238; 570/239; 570/262; 570/263
[58] Field of Search ........................... 570/177, 178, 570/179, 180, 211, 213, 238, 239, 262, 263; 585/310, 312, 733

[56] References Cited

U.S. PATENT DOCUMENTS

| | | |
|---|---|---|
| 4,895,995 | 1/1990 | James et al. |
| 5,013,424 | 5/1991 | James, Jr. et al. ............ 208/78 |

*Primary Examiner*—Alan Siegel
*Attorney, Agent, or Firm*—Thomas K. McBride; John G. Tolomei; John G. Cutts, Jr.

[57] ABSTRACT

A process for the conversion of a halogenated organic stream containing trace quantities of organic nitrates to produce a stream comprising hydrogenated hydrocarbonaceous compounds free from organic nitrates and halogenated organic compounds by means of contacting the feed stream and hydrogen with a selective hydrogenation catalyst in a first hydrogenation zone at hydrogenation conditions to convert the organic nitrates into water-soluble nitrogen compounds while effectively minimizing the production of hydrogen halide compounds. The resulting effluent from the first hydrogenation zone is contacted with an aqueous scrubbing solution to recover at least a portion of the water-soluble nitrogen compounds in order to produce a stream containing halogenated organic compounds and essentially free of nitrogen compounds which is then introduced into a second hydrogenation zone operated at selected hydrogenation conditions to produce water-soluble hydrogen halide compounds and hydrogenated hydrocarbonaceous compounds.

9 Claims, 1 Drawing Sheet

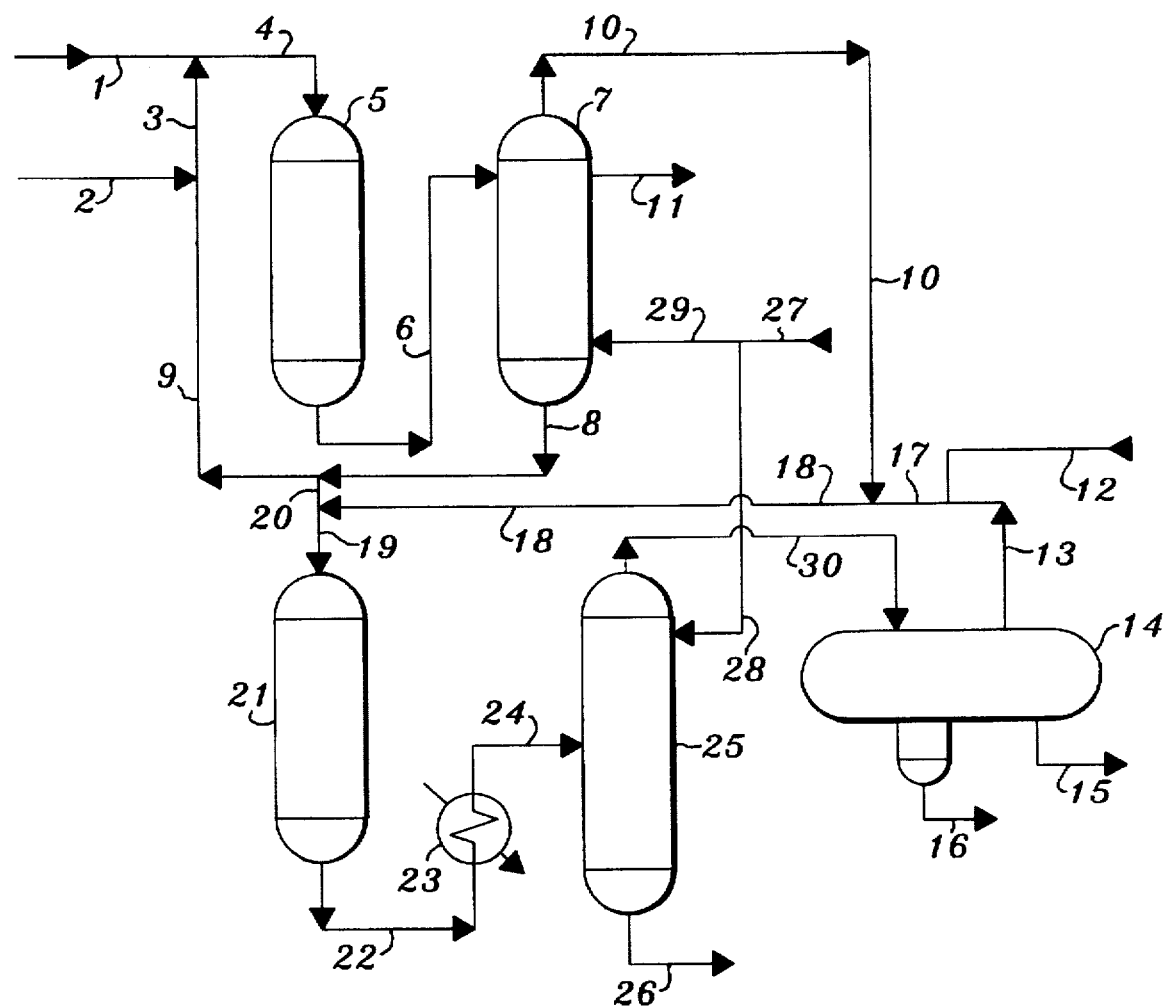

5,744,669

PROCESS FOR THE CONVERSION OF A HALOGENATED ORGANIC STREAM CONTAINING TRACE QUANTITIES OF ORGANIC NITRATES

CROSS-REFERENCE TO RELATED APPLICATION

This is a continuation-in-part of application Ser. No. 08/388,112 filed Feb. 13, 1995 now U.S. Pat. No. 5,600,041, which is a continuation-in-part of application Ser. No. 08/192,532 filed on Feb. 7, 1994, now abandoned, which is a continuation-in-part of application Ser. No. 07/981,962 filed on Nov. 25, 1992, now abandoned, all of which are incorporated by reference.

FIELD OF THE INVENTION

The field of art to which this invention pertains is the conversion of a halogenated organic stream containing trace quantities of organic nitrates to produce a stream comprising hydrogenated hydrocarbonaceous compounds essentially free from organic nitrates and halogenated organic compounds. More specifically, the invention relates to a process for treating a stream containing halogenated organic compounds and having trace quantities of organic nitrates to produce a stream comprising hydrogenated hydrocarbonaceous compounds free from organic nitrates and halogenated organic compounds by the utilization of a multi-stage hydrogenation zone operated at a first set of selective hydrogenation conditions in order to convert the organic nitrates to water-soluble nitrogen compounds while minimizing the hydrodehalogenation of the halogenated organic compounds and a second set of selective hydrogenation conditions for the conversion of the halogenated organic compounds to produce a stream containing hydrogenated hydrocarbonaceous compounds essentially free of halogenated organic compounds.

BACKGROUND OF THE INVENTION

In U.S. Pat. No. 5,013,424 (James, Jr. et al), a process is disclosed wherein a feedstock comprising halogenated organic compounds is contacted with hydrogen in a hydrogenation reaction zone to produce hydrocarbonaceous compounds and at least one water-soluble inorganic halide compound. The '424 patent contemplates processing a feedstock which is free of contaminating organic nitrates which would complicate the operation of the process to produce at least one water-soluble inorganic halide compound. The main thrust of the '424 patent is to essentially convert all of the halide compounds into water-soluble inorganic halide compounds. In the event that the feed to the '424 patent contains significant quantities of organic nitrates, the resulting hydrogen halide compound which is produced would be contaminated by water-soluble nitrogen compounds and its value would thereby be decreased. In addition, the water-soluble nitrogen compounds would react with the co-produced hydrogen halide to form ammonium chloride which forms deposits in the processing plant when the hydrogenation zone effluent is cooled.

Recent developments in the treatment of halogenated organic compounds has created a demand for technology which is capable of treating a stream containing halogenated organic compounds and organic nitrates. With the increased environmental emphasis for the treatment and recycle of waste streams containing organic compounds, there is an increased need for improved processes to accomplish such treatment and recycle. For example, during the disposal or recycle of potentially harmful hydrocarbonaceous waste streams, an important step in the total solution to the problem is the pretreatment or conditioning of an organic stream which facilitates the ultimate resolution to produce product streams which may subsequently be handled in an environmentally acceptable manner. Therefore, those skilled in the art have sought to find feasible techniques to convert a stream containing halogenated organic compounds and organic nitrate compounds to produce a stream comprising hydrogenated hydrocarbonaceous compounds free from organic nitrates and halogenated organic compounds.

It has recently been discovered that when a feedstock comprising halogenated organic compounds and relatively small quantities of organic nitrate compounds is processed to produce water-soluble inorganic halide compounds, several problems are encountered as a result of the conversion of organic nitrate compounds to ammonia and subsequently ammonium chloride. These problems include the need for higher operating temperatures to maintain inorganic halide production, the undesirable contamination of the inorganic halide compound product stream with nitrogen compounds and the plating out of ammonium chloride on the cooler surfaces of the plant as the reactor effluent is cooled in preparation for subsequent separation and product recovery. In many cases, the recovered inorganic halide compound product stream is recycled to production facilities, such as chlorine production, for example, which require high-purity halide compounds without nitrogen contaminants. The removal of trace quantities of organic nitrates from a stream containing halogenated organic compounds is problematic because the organic nitrates cannot be simply removed by water wash or other separation techniques.

BRIEF SUMMARY OF THE INVENTION

The present invention provides a process to produce a stream comprising hydrogenated hydrocarbonaceous compounds essentially free from organic nitrates and halogenated organic compounds from a stream comprising halogenated organic compounds and organic nitrates by means of contacting the feed stream and hydrogen with selective hydrogenation catalyst in a first hydrogenation zone at hydrogenation conditions to convert the organic nitrates into water-soluble nitrogen compounds while effectively minimizing the production of hydrogen halide compounds. The resulting effluent from the first hydrogenation zone is contacted with an aqueous scrubbing solution to recover at least a portion of the water-soluble nitrogen compounds in order to produce a stream containing halogenated organic compounds and essentially free of nitrogen compounds which is then introduced into a second hydrogenation zone operated at selected hydrogenation conditions to produce water-soluble hydrogen halide compounds and hydrogenated hydrocarbonaceous compounds. Important elements of the process are the ability to produce a stream containing hydrogenated hydrocarbonaceous compounds essentially free of organic nitrates and halogenated organic compounds thereby permitting the subsequent recovery and use. The water-soluble hydrogen halide compounds can be readily separated and recovered for further use. In accordance with the present invention, "essentially free of organic nitrates" means preferably containing less than about 20 ppm nitrogen and more preferably less than about 10 ppm nitrogen. The present invention enjoys the advantage of converting a stream containing halogenated organic compounds and trace quantities of organic nitrogen compounds in a convenient and economical manner. The results of this advantage include the maximum production and recovery of high purity hydrogen halide and the hydrocarbonaceous compounds, reduced operating costs, and better on-stream efficiency.

One embodiment of the invention may be characterized as a process for the conversion of a stream comprising halogenated organic compounds and trace quantities of organic nitrates which process comprises: (a) contacting the stream comprising halogenated organic compounds and trace quantities of organic nitrates, and hydrogen with a selective hydrogenation catalyst comprising a refractory inorganic oxide and at least one metallic compound having hydrogenation activity and selected from the group consisting of Group VIB and VIII of the Periodic Table in a first hydrogenation zone at hydrogenation conditions including a pressure from about atmospheric to about 2000 psig, a temperature from about 60° F. to about 212° F., a liquid hourly space velocity from about 0.05 $hr^{-1}$ to about 20 $hr^{-1}$ and a hydrogen to feed ratio from about one to about 1,000 SCFB selected to produce at least one water-soluble nitrogen compound while minimizing the production of hydrogen halide compounds; (b) contacting the resulting effluent from the first hydrogenation zone comprising hydrogen, halogenated organic compounds and water-soluble nitrogen compounds with an aqueous scrubbing solution to absorb at least a portion of the water-soluble nitrogen compounds to produce a first hydrogen-rich gaseous stream, an aqueous stream comprising water-soluble nitrogen compounds and a stream comprising halogenated organic compounds having less than about 20 ppm nitrogen; (c) contacting the stream comprising halogenated organic compounds having less than about 20 ppm nitrogen with hydrogen in a second hydrogenation reaction zone operated at hydrogenation conditions selected to produce hydrogenated hydrocarbonaceous compounds and to generate at least one water-soluble hydrogen halide compound; (d) contacting the resulting effluent from the second hydrogenation zone comprising hydrogenated hydrocarbonaceous compounds, a hydrogen-rich gas and at least one water-soluble hydrogen halide compound with a halide-lean absorber solution in an absorption zone; (e) withdrawing a halide-rich absorber solution containing at least a portion of the water-soluble hydrogen halide compound from the absorption zone; (f) withdrawing a stream comprising hydrogenated hydrocarbonaceous compounds and a hydrogen-rich gas from the absorption zone; and (g) introducing the stream recovered in step (f) into a separation zone to produce a second hydrogen-rich gaseous stream and a hydrogenated hydrocarbonaceous stream.

Other embodiments of the present invention encompass further details such as preferred feedstocks, hydrogenation catalysts, and operating conditions, all of which are hereinafter disclosed in the following discussion of each of these facets of the invention.

BRIEF DESCRIPTION OF THE DRAWING

The drawing is a simplified process flow diagram of a preferred embodiment of the present invention.

DETAILED DESCRIPTION OF THE INVENTION

The present invention provides an improved process for the conversion of a halogenated organic stream containing halogenated organic compounds and organic nitrates to produce hydrogenated hydrocarbonaceous compounds and hydrogen halide compounds. A wide variety of organic streams containing halogenated organic compounds and organic nitrates are to be candidates for feed streams in accordance with the process of the present invention. Examples of organic streams which are suitable for treatment by the process of the present invention are halogenated by-products from propylene oxide, epichlorohydrin, acetaldehyde, vinyl chloride monomer, brominated phenol and bisphenol, synthetic refrigerants and other similar chemical production plants as well as spent halogenated solvents and residues derived from the recycle of such solvents. The organic nitrates are preferably present in the feedstock in an amount from about 20 wppm to about 2 weight percent. The halogenated organic compounds are preferably present in the feedstock in an amount from about 1 to about 99 weight percent.

In accordance with the subject invention, a feed stream comprising halogenated organic compounds and organic nitrates is contacted in the presence of hydrogen with a selective hydrogenation catalyst in a hydrogenation zone at hydrogenation conditions selected to produce at least one water-soluble nitrogen compound while minimizing the production of hydrogen halide compounds. The water-soluble nitrogen compound is preferably selected from the group consisting of ammonia, ammonium chloride, primary amines, secondary amines, tertiary amines, and nitriles. The catalytic hydrogenation zone may contain a fixed, ebullated or fluidized catalyst bed. This reaction zone is preferably maintained under an imposed pressure from about atmospheric (0 kPa gauge) to about 2,000 psig (13790 kPa gauge) and more preferably under a pressure from about 100 psig (689.5 kPa gauge) to about 1000 psig (6895 kPa gauge). Suitably, such reaction is conducted with a maximum catalyst bed temperature in the range of about 60° F. (15° C.) to about 212° F. (100° C.) selected to produce at least one water-soluble nitrogen compound while minimizing the production of hydrogen halide compounds. In accordance with the present invention, it is contemplated that the desired hydrogenation conversion includes primarily the selective conversion of water-insoluble organic nitrates. As used herein, the expression "organic nitrates" refers to water-insoluble compounds containing nitrogen. Preferred organic nitrates are selected from the group consisting of methyl nitrate and chloropropyl nitrate. Hydrogen is present in the hydrogenation zone in an amount at least great enough to satisfy the stoichiometric hydrogen required for the selective conversion of organic nitrates. Hydrogen may also be added on a once-through gas phase basis or dissolved in the liquid feed. Further preferred operating conditions include liquid hourly space velocities in the range from about 0.05 $hr^{-1}$ to about 20 $hr^{-1}$ and hydrogen to feed ratios from about 1 standard cubic feet per barrel (SCFB) (0.17 normal $m^3/m^3$) to about 1000 SCFB (168 normal $m^3/m^3$), preferably from about 10 SCFB (1.68 normal $m^3/m^3$) to about 500 SCFB (84 normal $m^3/m^3$) when hydrogen circulation is used.

The preferred catalytic composite disposed within the hereinabove described hydrogenation zone can be characterized as containing a metallic component having hydrogenation activity, which component is combined with a suitable refractory inorganic oxide carrier material or carbon-based material of either synthetic or natural origin. The precise composition and method of manufacturing the carrier material is not considered essential to the present invention. Preferred carrier materials are alumina, silica and mixtures thereof. Suitable metallic components having hydrogenation activity are those selected from the group comprising the metals of Groups VI-B and VIII of the Periodic Table, as set forth in the *Periodic Table of the Elements*, E. H. Sargent and Company, 1964. Thus, the catalytic composites may comprise one or more metallic components from the group of molybdenum, tungsten, chromium, iron, cobalt, nickel, platinum, palladium, iridium, osmium, rhodium, ruthenium, and mixtures thereof. The concentration of the catalytically active metallic component, or components, is primarily dependent upon a particular metal as well as the physical and/or chemical characteristics of the particular hydrocarbon feedstock. For example, the metallic components of Group VI-B are generally present in an amount within the range of about 1 to about 20 weight percent, the iron-group metals in an amount within the range of about 0.2 to about 10 weight percent, whereas the noble metals of Group VIII are preferably present in an amount within the range of about 0.1 to about 5 weight percent, all of which are calculated as if these components existed within the catalytic composite in the elemental state. In accordance with a preferred embodiment of the present invention, the preferred catalysts contain alumina and palladium. It is further contemplated that hydrogenation catalytic composites may comprise one or more of the following components: cesium, francium, lithium, potassium, rubidium, sodium, copper, gold, silver, cadmium, mercury and zinc.

The resulting effluent from the selective hydrogenation zone is, in one embodiment, preferably admitted to a separation zone which is maintained at essentially the same pressure as the hydrogenation zone wherein a hydrogen-rich gaseous phase is produced and recycled to the hydrogenation zone. A liquid phase is removed from the separation zone and is contacted with an aqueous scrubbing solution and the resulting admixture is introduced into a second separation zone in order to produce a gaseous stream, a halogenated organic stream having less than about 20 ppm nitrogen and a spent aqueous stream. The contact of the effluent from the first separation zone with the aqueous scrubbing solution may be performed in any convenient manner and is preferably conducted by co-current, in-line mixing which may be promoted by inherent turbulence, mixing orifices or any other suitable mixing means. The aqueous scrubbing solution is preferably introduced in an amount from about 0.05 to about 200 vol. % based on the liquid effluent from the first separation zone. The aqueous scrubbing solution is selected depending on the characteristics of the original feedstock. In accordance with the present invention, the feedstock comprises halogenated compounds and the aqueous scrubbing solution preferably contains an acid compound such as hydrogen chloride to absorb the water-soluble nitrogen compounds which are produced in the first selective hydrogenation zone. In another embodiment, the effluent from the first selective hydrogenation zone may be scrubbed with an aqueous solution and separated into phases in a single zone or vessel.

At least a portion of the halogenated organic stream having less than about 20 ppm nitrogen is introduced into a second catalytic hydrogenation zone together with a hydrogen-rich gaseous stream which zone is maintained at hydrogenation conditions selected to produce hydrocarbonaceous compounds and hydrogen halide. This catalytic hydrogenation zone may contain a fixed, ebullated or fluidized catalyst bed. The operating conditions selected for this second catalytic hydrogenation zone are selected primarily to dehalogenate the halogenated organic compounds. This catalytic hydrogenation zone is preferably maintained under an imposed pressure from about atmospheric to abbot 2000 psig (13790 kPa gauge) and more preferably under a pressure from about 100 psig (689.5 kPa gauge) to about 1800 psig (12411 kPa gauge). Suitably, such reaction is conducted with a maximum catalyst bed temperature in the range of about 122° F. (50° C.) to about 850° F. (454° C.) selected to perform the desired dehalogenation conversion to reduce or preferably eliminate the concentration of halogenated organic compounds contained in the combined feed stream. Further preferred operating conditions include liquid hourly space velocities in the range from about 0.05 $hr^{-1}$ to about 20 $hr^{-1}$ and hydrogen circulation rates from about 200 standard cubic feet per barrel (SCFB) (33.71 normal $m^3/m^3$) to about 100,000 SCFB (16851 normal $m^3/m^3$), preferably from about 200 SCFB (33.71 normal $m^3/m^3$) to about 50,000 SCFB (8427 normal $m^3/m^3$).

In a preferred embodiment of the present invention, at least a portion of the hydrogen-rich gaseous stream which is introduced into the first and/or second hydrogenation reaction zone is provided via a recycle stream which is recovered from one or both of the hydrogenation zones.

In the event that the temperature of the feed to the hydrogenation reaction zone is not deemed to be exactly the temperature selected to achieve the selected conversions, it is contemplated that the temperature of the feed stream may be adjusted either upward or downward in order to achieve the desired temperature in the catalytic hydrogenation zone. Such temperature adjustment may be accomplished, for example, by either indirect heat exchange or by the addition of either cool or hot hydrogen.

Either of the hydrogenation zones utilized in the present invention may contain one or more catalyst zones. The preferred catalytic composites disposed within the hydrogenation zones which are utilized to hydrogenate the feed can be selected from the preferred catalytic composites which have been described hereinabove.

The hydrocarbonaceous effluent from the second hydrogenation zone utilized to hydrogenate the feed comprising halogenated organic compounds is preferably contacted with an aqueous halide-lean absorber solution and separated to produce a halide-rich aqueous stream, a hydrogenated hydrocarbonaceous liquid phase and a hydrogen-rich gaseous phase. The contact of the hydrocarbonaceous effluent from the second hydrogenation zone with the aqueous halide-lean absorber solution may be performed in any convenient manner and is preferably conducted by co-current, in-line mixing which may be promoted by inherent turbulence, mixing orifices or any other suitable mixing means. The aqueous halide-lean absorber solution is preferably introduced in an amount from about 1 to about 100 volume percent of the total feedstock charged to the second hydrogenation zone based on the quantity of hydrogen halide compounds present in the effluent from the second hydrogenation zone. The aqueous halide-lean absorber solution is selected depending on the characteristics of the organic feed stream introduced into the second hydrogenation zone. In accordance with the present invention, at least some halogenated organic compounds are introduced as feedstock and therefore the aqueous halide-lean absorber solution in one embodiment preferably contains a basic compound such as calcium hydroxide, potassium hydroxide or sodium hydroxide in order to neutralize the acid such as hydrogen chloride, hydrogen bromide and hydrogen fluoride, for example, which is formed during the hydrogenation of the halogenated organic compounds. In another preferred embodiment, the hydrogen halide component is recovered by dissolution in water or a lean aqueous solution of the halide compound. This embodiment permits the subsequent recovery and use of a desirable and valuable hydrogen halide compound. The final selection of the aqueous halide-lean absorber solution is dependent upon the particular halide compounds which are present and the desired end product. The resulting hydrogenated hydrocarbonaceous liquid phase is recovered and the hydrogen-rich gaseous phase is recycled in one embodiment.

In accordance with the present invention, it is preferred that the hydrogenated hydrocarbonaceous liquid phase comprising hydrogen and low molecular weight normally gaseous hydrocarbons be stabilized in a convenient manner, such as, for example, by stripping or flashing to remove the normally gaseous components to provide a stable hydrogenated distillable hydrocarbonaceous product. In some cases, it is contemplated that a significant portion of the hydrogenated hydrocarbonaceous product may comprise methane, ethane, propane, butane, heptane, hexane and admixtures thereof. An adsorber/stripper arrangement may conveniently be used to recover methane and ethane. Fractionation may conveniently be used to produce purified product streams such as liquid propane or LPG containing propane and butane.

In the drawing, the process of the present invention is illustrated by means of a simplified flow diagram in which such details as pumps, instrumentation, heat-exchange and heat-recovery circuits, compressors and similar hardware have been deleted as being non-essential to an understanding of the techniques involved. The use of such equipment is well within the purview of one skilled in the art.

DETAILED DESCRIPTION OF THE DRAWING

With reference now to the drawing, a liquid hydrocarbonaceous stream comprising halogenated organic compounds and trace quantities of organic nitrates is introduced into the process via conduit 1 and is admixed with a stream comprising hydrogen and a liquid recycle stream containing organic halide compounds which are transported via conduit 3. The resulting admixture is carried via conduit 4 and introduced into hydrogenation zone 5. The resulting effluent from hydrogenation zone 5 containing halogenated organic compounds and a water-soluble nitrogen compound is introduced into wash column 7 via conduit 6. A lean aqueous scrubbing solution is introduced via conduits 27 and 29 into wash column 7. A rich aqueous solution containing a dissolved water-soluble nitrogen compound is removed from wash column 7 via conduit 11. A hydrogen-rich gaseous stream is removed from wash column 7 via conduit 10. A liquid stream containing halogenated organic compounds is removed from wash column 7 via conduit 8 and at least a portion is recycled via conduits 9 and 3 as described hereinabove. Another portion is transported via conduit 20, admixed with a hydrogen-rich gaseous stream supplied via conduit 18 and the resulting admixture is introduced via conduit 19 into hydrogenation zone 21. A resulting effluent from hydrogenation zone 21 and containing hydrogenated hydrocarbonaceous compounds and hydrogen halide compounds is removed via conduit 22 and introduced into heat-exchanger 23. The resulting cooled effluent from heat-exchanger 23 is transported via conduit 24 and introduced into absorber 25. A halide-lean absorber solution is transported via conduits 27 and 28 and introduced into absorber 25. A halide rich aqueous absorption stream is removed from absorber 25 via conduit 26. A stream containing hydrogen and hydrogenated hydrocarbonaceous compounds is removed from absorber 25 via conduit 30 and introduced into vapor-liquid separator 14. A hydrogen-rich gaseous stream is removed from vapor-liquid separator 14 via conduit 13 and admixed with makeup hydrogen introduced via conduit 12 and the resulting admixture is transported via conduit 17 and is admixed with a previously recovered hydrogen-rich gaseous stream transported via conduit 10 and the resulting admixture is transported via conduit 18 and introduced into hydrogenation zone 21 as described hereinabove. A liquid stream containing hydrogenated hydrocarbonaceous compounds is removed from vapor-liquid separator 14 via conduit 15 and recovered. An aqueous stream is removed from vapor-liquid separator 14 via conduit 16 and recovered. Fresh makeup hydrogen is supplied via conduit 2 and is introduced into hydrogenation zone 5 via conduits 3 and 4 as described hereinabove.

EXAMPLE 1

A feed stream containing chlorinated by-products from a propylene oxide production plant having the characteristics presented in Table 1 was charged at a rate of 100 mass units per hour to a hydrogenation zone containing a hydrogenation catalyst containing alumina and palladium, and operated at conditions including a pressure of 750 psig, a hydrogen circulation rate of 40,000 SCFB and a catalyst peak temperature of about 572° F. (300° C.). The object of this example is to hydrogenate the chlorinated organic compounds to produce hydrocarbons and hydrogen chloride. After the hydrogenation zone was operated for about 35 days, the reactor circuit started to develop increasing pressure drop which indicated partial plugging and the activity of the catalyst was observed to prematurely decline. The plant was subsequently shut down and the hydrogenation zone outlet piping was inspected and found to contain significant deposits of ammonium chloride. Before the plant was shut down, a resulting liquid product was recovered from the effluent of the hydrogenation zone in an amount of about 100 mass units per hour and having the characteristics presented in Table 2.

TABLE 1

| CHLORINATED BY-PRODUCT FEEDSTOCK ANALYSIS | |
|---|---|
| Dichloropropane, weight percent | 90 |
| Epichlorohydrin, weight percent | 1 |
| Dichloropropyl Ether, weight percent | 8.9 |
| Chloropropyl Nitrate, weight percent | ~0.1 |
| Total Nitrogen, weight ppm | ~100 |

TABLE 2

| HYDROGENATION ZONE EFFLUENT ANALYSIS, WEIGHT PERCENT OF FEED | |
|---|---|
| Hydrogen Chloride | 63.9 |
| Propane | 38.7 |
| Other | 0.9 |
| Total | 103.5 |

After the premature plant shutdown was experienced, the feed was inspected and analyzed and it was determined that the feed unexpectedly contained low quantities of organic nitrate compounds which were found to be soluble in the feed and not extractable with common extraction solvents. This example represents the prior art and demonstrates the difficulties in attempting to hydrogenate a stream containing chlorinated organic compounds which unexpectedly contained trace quantities of organic nitrates.

EXAMPLE 2

This example was performed in accordance with the present invention. A feed stream containing chlorinated by-products from a propylene oxide production plant having the characteristics presented in Table 1 was charged at a rate of 100 mass units per hour to a hydrogenation zone containing a hydrogenation catalyst containing alumina and palladium, and operated at conditions including a pressure of 200 psig (1379 kPa gauge), a hydrogen to feed ratio of 300 SCFB (84.3) m$^3$/m$^3$ and a catalyst peak temperature of about 95° F. (35° C.). These operating conditions were selected to convert the organic nitrate compounds to water-soluble nitrogen compounds while minimizing the production of hydrogen halide compounds. These conditions are less severe than those used in Example 1 and were selected in accordance with the present invention.

A resulting liquid product was recovered from the effluent of the hydrogenation zone in an amount of about 100 mass units per hour and was water washed to extract the water-soluble nitrogen compounds. The resulting water washed liquid was found to have the characteristics presented in Table 3.

TABLE 3

| HYDROGENATION ZONE LIQUID EFFLUENT ANALYSIS | |
| --- | --- |
| Dichloropropane, weight percent | 90 |
| Epichlorohydrin, weight percent | 0.1 |
| Dichloropropyl Ether, weight percent | 9 |
| Chloropropyl Nitrate, weight percent | 0.01 |
| Chlorinated Propanol, weight percent | 0.9 |
| Total Nitrogen, weight ppm | <10 |

EXAMPLE 3

The conversion process described in Example 1 was repeated with the exception that a feed having the characteristics presented in Table 3 was used. A resulting product recovered from the effluent of the hydrogenation zone was essentially the same as shown in Table 2.

The plant was continuously operated for about 60 days without any detectable increased pressure drop and the catalyst stability was observed to be superior to that in Example 1.

The foregoing description, drawing and examples clearly illustrate the advantages encompassed by the process of the present invention and the benefits to be afforded with the use thereof.

What is claimed:

1. A process for the conversion of a stream comprising halogenated organic compounds and trace quantities of organic nitrates which process comprises:

(a) contacting said stream comprising halogenated organic compounds and said trace quantities of organic nitrates, and hydrogen with a selective hydrogenation catalyst comprising a refractory inorganic oxide and at least one metallic compound having hydrogenation activity and selected from the group consisting of Group VIB and VIII of the Periodic Table in a first hydrogenation zone at hydrogenation conditions including a pressure from about atmospheric to about 2000 psig, a temperature from about 60° F. to about 212° F., a liquid hourly space velocity from about 0.05 hr$^{-1}$ to about 20 hr$^{-1}$ and a hydrogen to feed ratio from about one to about 1,000 SCFB selected to produce at least one water-soluble nitrogen compound while minimizing the production of hydrogen halide compounds;

(b) contacting the resulting effluent from said first hydrogenation zone comprising hydrogen, halogenated organic compounds and water-soluble nitrogen compounds with an aqueous scrubbing solution to absorb at least a portion of said water-soluble nitrogen compounds to produce a first hydrogen-rich gaseous stream, an aqueous stream comprising water-soluble nitrogen compounds and a stream comprising halogenated organic compounds having less than about 20 ppm nitrogen;

(c) contacting said stream comprising halogenated organic compounds having less than about 20 ppm nitrogen with hydrogen in a second hydrogenation reaction zone operated at hydrogenation conditions selected to produce hydrogenated hydrocarbonaceous compounds and to generate at least one water-soluble hydrogen halide compound;

(d) contacting the resulting effluent from said second hydrogenation zone comprising hydrogenated hydrocarbonaceous compounds, a hydrogen-rich gas and at least one water-soluble hydrogen halide compound with a halide-lean absorber solution in an absorption zone;

(e) withdrawing a halide-rich absorber solution containing at least a portion of said water-soluble hydrogen halide compound from said absorption zone;

(f) withdrawing a stream comprising hydrogenated hydrocarbonaceous compounds and a hydrogen-rich gas from said absorption zone; and (g) introducing said stream recovered in step (f) into a separation zone to produce a second hydrogen-rich gaseous stream and a hydrogenated hydrocarbonaceous stream.

2. The process of claim 1 wherein said stream comprising halogenated organic compounds and organic nitrates is selected from the group consisting essentially of halogenated by-products from propylene oxide, epichlorohydrin, acetaldehyde, brominated phenol and bisphenol, synthetic refrigerant and vinyl chloride monomer production plants, spent halogenated solvents and residues derived from the recycle of such solvents.

3. The process of claim 1 wherein said hydrogenation catalyst contained in said first hydrogenation zone comprises alumina and palladium.

4. The process of claim 1 wherein said hydrogenation catalyst contained in said second hydrogenation zone comprises alumina and palladium.

5. The process of claim 1 wherein said organic nitrates are present in said stream comprising halogenated organic compounds in an amount from about 20 wppm to about 2 weight percent.

6. The process of claim 1 wherein said stream comprising halogenated organic compounds contains halogenated organic compounds in an amount from about 1 to about 99 weight percent.

7. The process of claim 1 wherein said aqueous scrubbing solution is introduced in an amount from about 0.05 to about 200 volume percent based upon the liquid effluent from said first hydrogenation zone.

8. The process of claim 1 wherein said halide-lean absorber solution is introduced in an amount from about 1 to about 200 volume percent based upon the liquid effluent from said second hydrogenation zone.

9. The process of claim 1 wherein said second hydrogenation zone is operated at hydrogenation conditions including a pressure from about 100 psig (689.5 kPa gauge) to about 1800 psig (12411 kPa gauge), a temperature from about 122° F. (50° C.) to about 850° F. (454° C.), a liquid hourly space velocity from about 0.05 hr$^{-1}$ to about 20 hr$^{-1}$ and a hydrogen circulation rate from about 200 SCFB (33.71 normal m$^3$/m$^3$) to about 50,000 SCFB (8427 normal m$^3$/m$^3$).

* * * * *